(12) United States Patent
Finarov

(10) Patent No.: US 7,245,375 B2
(45) Date of Patent: Jul. 17, 2007

(54) OPTICAL MEASUREMENT DEVICE AND METHOD

(75) Inventor: Moshe Finarov, Rehovot (IL)

(73) Assignee: Nova Measuring Instruments Ltd., Rehovot (IL)

(*) Notice: Subject to any disclaimer, the term of this patent is extended or adjusted under 35 U.S.C. 154(b) by 0 days.

(21) Appl. No.: 11/141,199

(22) Filed: Jun. 1, 2005

(65) Prior Publication Data

US 2005/0275845 A1    Dec. 15, 2005

(30) Foreign Application Priority Data

Jun. 1, 2004 (IL) ................................. 162290

(51) Int. Cl.
*G01J 4/00* (2006.01)
(52) U.S. Cl. .................................... 356/364
(58) Field of Classification Search .............. None
See application file for complete search history.

(56) References Cited

U.S. PATENT DOCUMENTS

| | | | |
|---|---|---|---|
| 5,604,344 A | 2/1997 | Finarov | |
| 5,682,242 A | 10/1997 | Eylon | |
| 5,887,590 A | 3/1999 | Price | |
| 6,122,051 A * | 9/2000 | Ansley et al. | 356/326 |
| 6,734,967 B1 | 5/2004 | Piwonka-Corle et al. | |
| 6,859,278 B1 * | 2/2005 | Johs et al. | 356/369 |
| 6,859,279 B1 | 2/2005 | Tabet | |
| 6,867,862 B2 | 3/2005 | Nikoonahad | |

FOREIGN PATENT DOCUMENTS

| | | |
|---|---|---|
| JP | 58039932 A1 | 3/1983 |
| WO | 02079760 A2 | 10/2002 |

OTHER PUBLICATIONS

U.S. Appl. No. 11/003,012.
R. M. Azzam et al "Ellipsometry and Polarized Light" (1986) pp. 364-411.
Masaki Yamamoto, "A New Type of Precision Ellipsometer without Employing a Compensator" Optics Communications, vol. 10, No. 2, (Feb. 1974) pp. 200-202.

* cited by examiner

*Primary Examiner*—Tu T. Nguyen
(74) *Attorney, Agent, or Firm*—Browdy and Neimark, PLLC

(57) ABSTRACT

A system and method are presented for measurement on an article. The system comprises an illuminator for producing light of at least one predetermined wavelength range; an optical system; a displacement arrangement; and a control system. The optical system is configured to define at least a measurement channel, and comprises a light directing assembly for directing an input light beam, propagating along an input light path from the illuminator, onto the article and directing a light beam returned from the illuminated region of the article to at least one light detector. The displacement arrangement is associated with at least the light directing assembly of the optical system, and is configured and operable by the control system to rotate said at least light directing assembly of the optical system with respect to a stage supporting the article about a rotational axis substantially normal to the stage.

28 Claims, 7 Drawing Sheets

OPTICAL MEASUREMENT DEVICE AND METHOD

FIELD OF THE INVENTION

This invention is generally in the field of optical measurement techniques and relates to an optical measurement device and method utilizing oblique angle spectrophotometric and ellipsometric measurements, particularly useful for measurements in patterned structures such as wafers in semiconductor industry.

BACKGROUND OF THE INVENTION

Ellipsometry is a well-known measurement technique for measuring polarization changes in a light beam caused by interaction with an article (i.e., reflection from or transmission through the article). Due to high accuracy of ellipsometric measurements and due to high sensitivity of ellipsometric parameters to thin films (articles), these measurements are widely used in different fields, including biological and medical applications, as well as electrochemistry and microelectronics. Ellipsometry has been used in the semiconductor industry to measure thickness of very thin films, such as silicon dioxide films, silicon nitride and the like, and thus to control critical processes of semiconductor manufacturing like thermal oxidation, chemical-vapor deposition, etc.

Spectrophotometric measurements (also termed reflectometry, spectrometry, scatterometry) are also widely used techniques for measuring thickness and optical properties of thin films and patterns in semiconductor manufacturing. Usually, spectrophotometry is applied for measuring of thicker films than ellipsometry, but spectrophotometry has substantial advantages in many aspects like a spot size, throughput, cost, etc.

Different types of spectrophotometers and ellipsometers are known in the art and disclosed for example in "Ellipsometry and Polarized Light", R. M. Azzam et al., 1986. Ellipsometric and spectrophotometer systems typically include a stationary optical head and an appropriate support assembly, for example having two-coordinate stage for holding and locating an article under measurement relative to a light spot.

The reflectometry and ellipsometry systems can be implemented to operate in both normal and oblique incidence of a light beam onto the article plane. The incidence plane (IP) is defined in space as a plane perpendicular to the article plane and including an incident light beam and a returned (e.g., reflected) beam. In case of optically isotropic articles, measurements are independent of the IP orientation relative to the article. In case of optically anisotropic articles, e.g. gratings, relative orientation of the IP and the article's features should be well defined in order to ensure correct measurement conditions.

Semiconductor wafers are typically in the form of an array of identical patterned regions (termed "die") arranged on a substrate. In case of a semiconductor wafer, if a measurement site within or near a die is a grating (line array) oriented along X- or Y-axis and a wafer is oriented on an X-Y-stage at a required angle relative to the IP, all such sites along the wafer surface are oriented at the same angle so measuring different sites by moving the stage from one location to another is carried out under the same conditions.

Recently, polar stages for wafer movement have been used in some optical systems mainly for reaching a small system footprint, allowing using them in integrated metrology (i.e., installing them into a limited space of processing equipment). In order to measure different sites on a wafer, the polar stage should move the wafer by both translation (R-coordinate) and rotation (Theta-coordinate). In this case, each measurement site will be oriented differently relative to the IP of the optical head of an oblique angle reflectometer or ellipsometer, thus not allowing the same measurement condition for anisotropic sites. For this reason, polar stages are typically used only with normal incidence measurement devices, while oblique incidence devices like ellipsometers utilize only X-Y-stages.

U.S. Pat. No. 6,859,279 discloses a method of measuring a small area on a substrate with an ellipsometer. According to this technique, a substrate is oriented with respect to the ellipsometer such that an elliptical light spot produced by the ellipsometer fits diagonally within the test area. Then, the surface properties of the substrate within the test area are measured with the ellipsometer.

SUMMARY OF THE INVENTION

There is a need in the art to facilitate oblique angle optical measurement by providing a novel optical monitoring system and method utilizing principles of reflectometry or ellipsometry, capable of operating with a compact polar stage for holding and moving an article (e.g., silicon wafer) under measurement, while enabling identical orientation of each anisotropic measurement site (e.g., grating) relative to the light incidence plane.

Here, the term "measurement" signifies any type of optical measurement, inspection or imaging.

The main idea of the invention is aimed at providing a simple configuration for rotating an incidence plane relative to the article in order to enable the required orientation of this plane for each measured site over the article. This is implemented by mounting a light directing optics, configured as a deflector of incident light and collector of returned light, for rotation about a rotational axis substantially normal to the article plane. This enables to obtain a required orientation of the incidence plane for each measured site over the article. The monitoring system of the invention is configured as an oblique incidence system enabling measurement/inspection of the article or also imaging/inspection of the article.

There is thus provided according to one broad aspect of the invention a system for measurement on an article, the system comprising:

(i) an illuminator for producing light of at least one predetermined wavelength range;

(ii) an optical system configured to define at least a measurement channel, the optical system comprising a light directing assembly for directing an input light beam, propagating along an input light path from the illuminator, onto the article and directing a light beam returned from the illuminated region of the article to at least one light detector;

(iii) a displacement arrangement associated with at least the light directing assembly of the optical system and configured and operable to rotate said at least light directing assembly of the optical system with respect to a stage supporting the article about a rotational axis substantially normal to the stage; and (iv) a control system configured and operable to control said displacement arrangement during the measurement.

The stage is preferably configured as an R-Theta stage.

Preferably, the displacement arrangement includes a rotatable holder configured for holding the at least light directing assembly of the optical system. The rotatable holder is preferably in the form of a hollow drum-like housing containing elements of the light directing assembly. The light detector may or may not be mounted inside the drum-like housing.

The light directing assembly is configured as a beam deflector assembly operable to provide a desired angle of incidence of the input light beam onto the measurement site. Preferably, the light directing assembly includes a reflective unit accommodated so as to be orientable in the input light path for deflecting the input light beam towards the measurement site. The reflection unit may include mirrors or one or more total internal reflection prism.

According to one embodiment of the invention, the reflective unit includes a first folding mirror mounted so as to be orientable in the input light path, and at least one second folding mirror accommodated so as to face by its reflective surface a reflective surface of the first folding mirror.

According to another embodiment of the invention, the reflective unit includes at least one total internal reflection prism for reflecting the input light beam towards the measurement site.

According to yet another embodiment of the invention, the reflective unit includes a first folding mirror mounted so as to be orientable in the input light path; at least one second folding mirror accommodated so as to face by its reflective surface a reflective surface of the first folding mirror; and a substantially spherical mirror oriented to reflect the returned light beam towards the same measurement spot to induce a second returned light beam propagating towards the second folding mirror.

According to yet another embodiment of the invention, the reflective unit includes a first folding mirror mounted so as to be orientable in the input light path; at least one second folding mirror accommodated so as to face by its reflective surface a reflective surface of the first folding mirror; a substantially plane mirror in a path of light reflected from the second folding mirror and propagating towards the measurement site; a first substantially spherical mirror oriented to reflect light, reflected from the substantially plane mirror, towards the measurement site and reflect returned light from the article onto the substantially plane mirror; and a second substantially spherical mirror oriented to reflect the returned light beam towards the same measurement spot to induce a second returned light beam propagating towards the first spherical mirror.

The light directing assembly may include at least one lens arrangement configured for focusing the input light beam onto the measurement site, and/or collecting the returned light to direct it towards the light detector.

The optical system may include a beam separator unit accommodated in the light input path to direct the input light beam towards the light directing assembly and direct the returned light beam to the at least one light detector.

In some examples of the invention, the optical system includes a light guide accommodated upstream of the light detector. The light guide is configured to be highly reflective with respect to the at least one wavelength range.

According to some embodiments of the invention, the light directing assembly includes a polarization unit accommodated to apply polarization rotation to the input light beam and the returned light beam. The polarization unit may include a polarizer accommodated in a path of the input light beam deflected towards the measurement site, and an analyzer accommodated in the returned light beam path propagating towards the light detector. Preferably, the polarization unit also includes a compensator, which is accommodated either in a path of the polarized input light propagating towards the measurement site, or in a path of the returned light propagating towards the analyzer. Preferably, at least one of the polarizer and the analyzer is mounted for rotation around an axis parallel to the respective light path.

According to some embodiments of the invention mentioned above, the light directing assembly includes a polarizer accommodated to apply polarization rotation to the input light beam and the further returned light beam.

The optical system may be configured to define also an imaging channel. In some embodiments of the invention, the optical system includes a beam separator unit accommodated in the light input path to direct the input light beam towards the light directing assembly and direct the returned light beam to an imaging detector.

In some embodiments of the invention, the beam separator unit is accommodated in the light input path outside the rotatable holder to direct the input light beam towards the light directing assembly and to direct the returned light beam emerging from the light directing assembly to an imaging detector.

The configuration may be such that at least one reflector element of the reflection unit is displaceable between its operative position being in the light beam input path and thus directing the input light along the measurement channel and its inoperative position being outside the light input path and thus allowing the input light beam propagation along the imaging channel.

The light directing assembly may include an objective lens arrangement accommodated in a path of the input light beam propagating along the imaging channel towards the article.

The optical system may include a second beam separator accommodated in a path of the returned light emerging from the first beam separator to direct first and second spatially separated portions of the returned light towards, respectively, the measuring and imaging detectors.

In some embodiments of the invention, the light directing assembly includes at least one optical device formed by a first folding reflector mounted on a central axis of the rotatable holder (drum) so as to be in the input light path, and at least one second folding reflector spaced-apart from the first reflector. The light directing assembly may include an array of the optical devices formed by an array of the second folding reflectors arranged in a spaced apart relationship along a circumference of the drum all associated with the same first reflector. In this case, the system can be operable with variable angles of light incidence onto the measurement site.

According to another broad aspect of the invention, there is provided a method for use in measurement on an article, the method comprising:

(i) providing an input light beam of at least one predetermined wavelength range, and directing the input light beam along an input light path;
  (ii) passing the input light towards a measurement site through a deflector assembly rotatable with respect to the article about a rotational axis substantially normal to the article plane and configured to provide a desired oblique angle of incidence of the input beam onto the measurement site; and
  (iii) directing a light beam returned from the article along an oblique return path to at least one light detector.

Preferably, the passing of the input light through the deflector assembly includes causing a double reflection of light from the same measurement site, thereby providing a certain level of sensitivity of measurements with a smaller spot size.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF EMBODIMENTS OF THE INVENTION

The present invention provides a simple monitoring technique enabling rotation of an incidence plane relative to an article under monitoring. This is implemented by mounting a light directing optics, configured as a deflector of incident light and collector of returned light, for rotation about a rotational axis substantially normal to the article plane.

Thus, the invention utilizes rotation of the incidence plane relative to the article. This enables to obtain a required orientation of the incidence plane for each measured site over the article. The monitoring system of the invention is configured as an oblique incidence system enabling measurement/inspection of the article or also imaging/inspection of the article.

More specifically, the invention is used for monitoring semiconductor wafers, and is therefore exemplified below with respect to this application, but it should be understood that the invention is not limited to this specific example.

Figure 1:
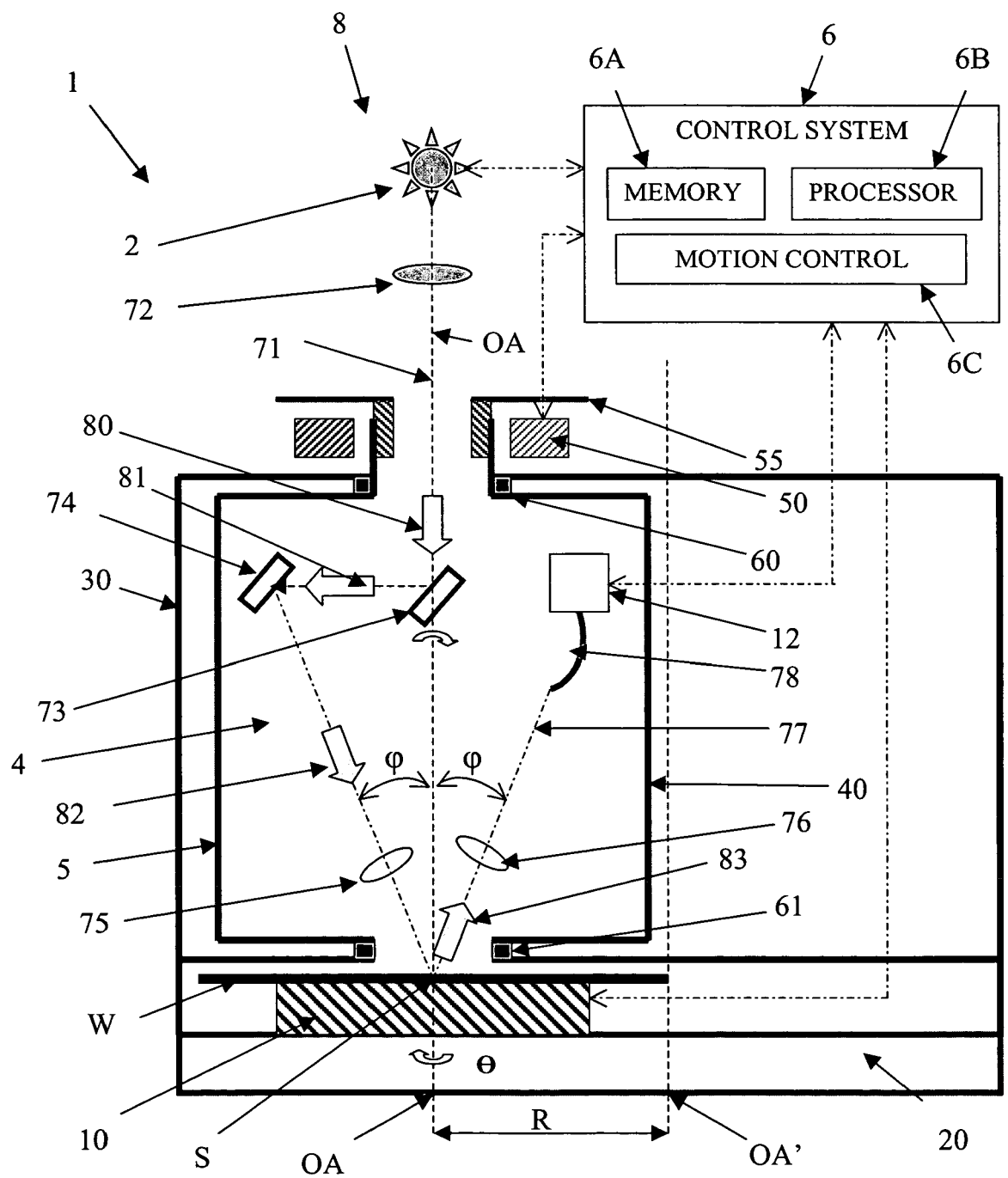
FIG. 1 is a schematic illustration of an example of a measurement system of the present invention.

Referring to FIG. 1, there is illustrated an example of a measurement system 1 of the present invention. In this example, the system 1 is configured as an oblique incidence reflectometer operable in a broad spectral range. The system 1 includes an illuminator 2, an optical system 4, a displacement arrangement 5, and a control system 6. The system 1 is associated with a stage 10 for supporting an article (e.g., wafer) W during measurements.

Preferably, stage 10 is configured as the so-called R-Theta stage, namely, moves the wafer W with respect to an incident light beam along two coordinates –R and θ. Optionally, the stage 10 can also be movable along a vertical axis Z in order to bring the wafer to the best focus of the optical system 4. In order to prevent contamination, movable parts of the stage 10 are typically located within an appropriate housing 20.

Illuminator 2 is configured and operable for producing light of at least one predetermined wavelength range. Illuminator 2 may be of any suitable type depending on the spectral range needed for performing spectrometric measurements. For visible to IR spectrum, a quartz-halogen lamp can be used, for example HLX 64621 commercially available from Osram. For UV to near IR spectrum, a Xenon lamp can be used, for example L 2193 commercially available from Hamamatsu, Japan. For DUV to visible spectral range, a Deuterium lamp can be used, for example L 6999-51 commercially available from Hamamatsu, Japan. It should be understood that any other illuminator (e.g., light emitting diodes, diode or gas lasers, etc.) may be used, as well as any combination of different light sources, for example as described in U.S. application Ser. No. 11/003,012, assigned to the assignee of the present application.

Optical system 4 is configured to define at least a measurement channel (and optionally also an imaging channel as will be exemplified further below). Optical system 4 includes a light directing assembly 8 for directing an input light beam 80, propagating along an input light path 71 from illuminator 2, onto a measurement spot S on wafer W and directing a light beam 83, returned from the illuminated spot along a returned path 77, to at least one light detector—one such detector 12 in the present example. Optical system 4 defines a reference optical axis OA which is substantially normal to stage 10 (i.e., to wafer W plane) and passes through the center of measurement spot S on the wafer W.

Displacement arrangement 5 is associated with at least light directing assembly 8 of optical system 4 and is configured and operable to rotate at least light directing assembly 8 with respect to stationary input light path 71 (stationary illuminator) about a rotational axis substantially normal to stage 10 (i.e., coinciding with the reference optical axis OA). In the present example, displacement arrangement 5 includes a rotatable holder 40, e.g., a drum, holding the elements of light directing assembly 8, holder 40 being accommodated in a top housing 30 rigidly connected to stage 10 (i.e., to bottom housing 20 of stage 10). Drum 40 is rotatable within bearings 60 and 61 at opposite sides of top housing 30. The drum rotation is operated by the control unit via a hollow-shaft motor assembly 50 (and using an angular encoder assembly 55). This enables to keep the rotational axis (substantially coinciding with the optical OA) constant in space during the drum rotation.

Light directing assembly 8 is configured as a beam deflector. This is implemented by providing a reflection unit, which in the present example includes a first folding mirror 73, at least one second folding mirror—one such mirror 74 in the present example, focusing and objective lens arrangements 75 and 76 (the provision of which is optional) in the optical path of incident and returned beams, respectively, and optionally includes a light guide 78 associated with detector 12. First mirror 73 is located on the rotational axis (central axis of drum 40) and is highly reflective for wavelengths of a specific spectral range used in the system.

It should be noted, although not specifically shown, that mirror 73 as well as other folding components can be replaced by a total internal reflection (TIR) prism enabling the highest possible reflectance, while being more expensive and bulky. It should also be understood that input light path 71 may be defined by an optical fiber connecting illuminator 2 to the inside of drum 40.

Also optionally provided in system 1 is a condenser lens arrangement 72, which in the present example is located outside the drum 40 (i.e., is stationary mounted).

Control system 6 is typically a computer system including inter alia a memory utility 6A, an appropriate processor utility 6B for transforming and transferring an output signal of detector 12 and processing and analyzing this signal to determine at least one parameter of the wafer (e.g., thickness), as well as a suitable motion control utility 6C for operating illuminator 2 and controlling the stage 10 and drum 40 movement.

Mounting the illuminator as a stationary assembly (i.e., outside the rotatable holder) is optimal from both the system performance and service ability standpoints. Accommodation of illuminator 2 outside rotatable holder 40 provides inter alia to overcome problems associated with the fact that the lifetime of any light source is typically limited and therefore easy access to the light source is needed to replace it; as well as the fact that any light source usually dissipates remarkable amount of heat that might affect closely located optical components.

System 1 operates in the following manner. Light produced by illuminator 2 propagates along input light path 71, is collected by condenser 72, and directed accurately along the optical axis OA as collimated light beam 80. Beam 80 enters rotatable light directing assembly 8 where it interacts with first mirror 73 resulting in a deflected beam 81 propagating towards second mirror 74 (or TIR prism). Beam 81 impinges on second mirror 74, and a reflected beam 82 propagates towards wafer W with an angle of incidence $\phi$ (i.e., an angle relative to optical axis OA normal to wafer W). In the present example, beam 82 passes through focusing lens arrangement 75 and thus produced small light spot S on the measurement site. Light beam 83 reflected from the illuminated site at the same angle $\phi$ is collected by objective lens arrangement 76 which projects the light spot along path 77 onto the entrance surface of light guide 78 connected to photo-detector 12.

Detector 12 is preferably a spectrometric multi-photo-diode detector, for example MMS-1 commercially available from Zeiss, Germany. It should be understood that any other appropriate light detector can be used, e.g., a charge-couple device (CCD), photovoltaic detector, photo-multiplier, etc. The photo-detector can include a grating, deviating light components of different wavelengths towards different elements of the detector (photo-diodes, CCD pixels, etc.).

The actual spot size on the detector is preferably defined by a ratio between the size of the entrance aperture of the detector (which is the diameter of the light guide 78 in the present example) and the optical magnification of objective lens 76. For example, if the entrance surface of light guide 78 is 0.5 mm and the magnification is 5×, the actual dimension of the measurement spot is 0.1 mm. It should be understood that this is the spot size in the direction perpendicular to the drawing plane. In the drawing plane, the spot size can be determined by a ratio between the above spot size and $\cos\phi$. For example, in this case and at $\phi=60°$, the spot size in the long direction is equal to 0.2 mm.

The incidence plane is defined by the axis of propagation of incident beam 82 and the axis of propagation of returned (reflected) beam 83, and normal axis OA, which is also the axis of the drum 40 rotation. A measurement point (the center of spot S) is a crossing point of these three axes. In order to orient the incidence plane relative to the desired measurement site on wafer W in the right direction, drum 40 is rotated about axis OA on an angle which is related to the angular site orientation, or in turn, to the wafer orientation angle $\theta$ in polar coordinates of R-$\theta$ stage 10.

It should be noted that during the drum rotation, none of the elements of optical system 4 (from light input path 71 to light output path 77) change its position relative to the other optical elements. Hence, from the optical standpoint, this scheme remains stationary, thus enabling high performance of measurements. Also, the center of measurement spot S on wafer W, does not move during the drum rotation, because the rotation axis and optical axis are substantially coinciding.

It should also be noted that the drum 40 rotation can be done simultaneously with the rotation and/or translation of wafer stage 10, while moving from one measurement point to another. Hence, such system configuration does not require additional measurement time as compared to the conventional systems.

In case of patterned articles, and when working with a small spot size, it is necessary to locate the light spot on the pre-selected measurement site within the pattern. Such positioning can be carried out by applying a suitable pattern recognition technique, for example as disclosed in U.S. Pat. Nos. 5,682,242 and 5,867,590, both assigned to the assignee of the present application.

Figure 2:
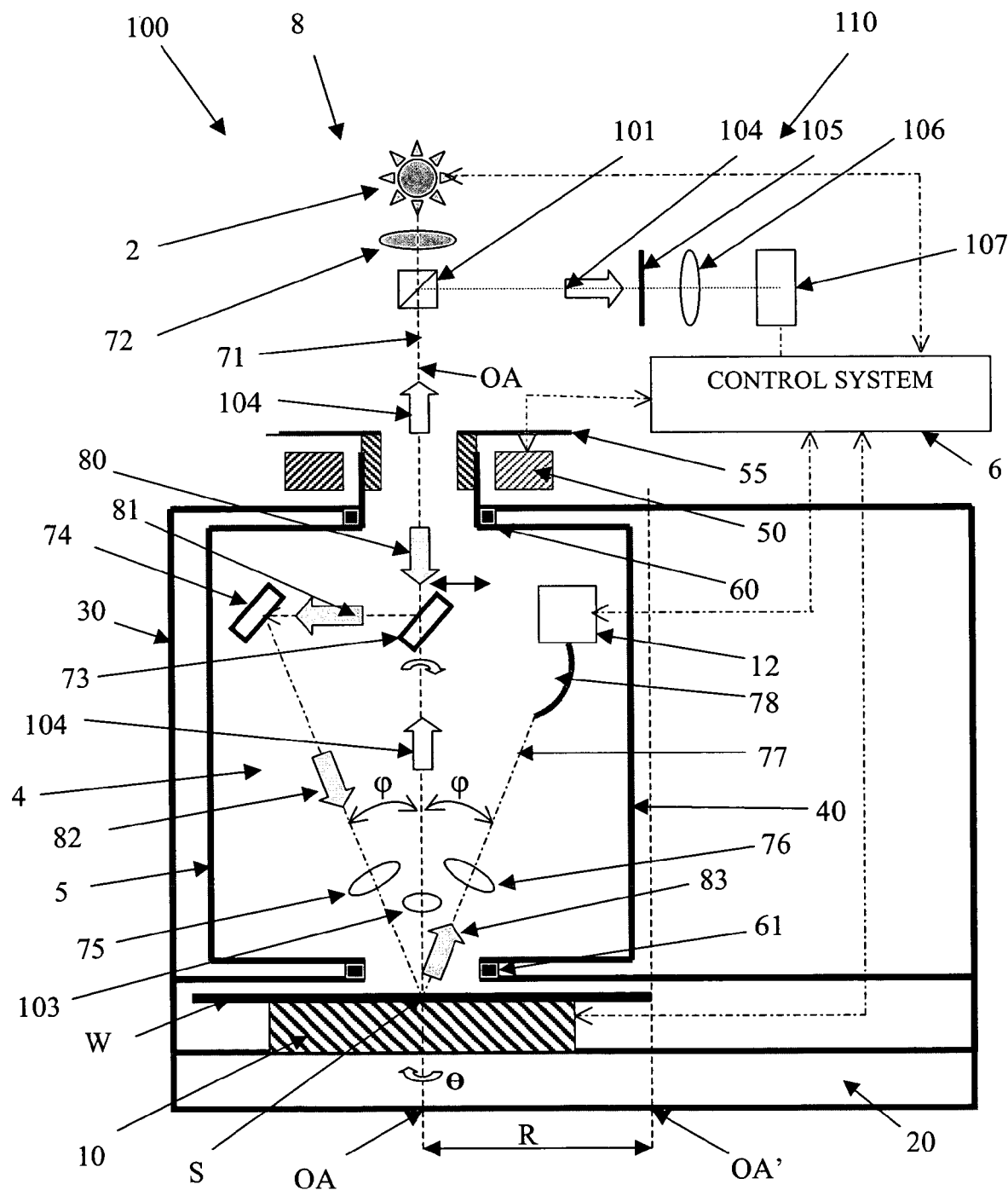
FIG. 2 schematically illustrates another example of a system of the present invention utilizing measurement and imaging channels.

In order to improve the pattern recognition capability, an imaging channel may additionally be used. This is exemplified in FIG. 2, showing schematically another example of a measurement system 100 of the present invention. To facilitate understanding, the same reference numbers are used for identifying components that are common in all the examples of the invention.

System 100 includes an illuminator 2, an optical system 4 that includes a light directing assembly 8 located inside a rotatable holder 40 (constituting a displacement arrangement 5), and a control system 6, and is associated with a wafer stage 10. An imaging channel is defined by a stationary imaging assembly 110 and an objective lens 103 located inside drum 40 and thus rotating with the drum. Also provided in optical system 4 is a beam-splitter 101 accommodated in a path of an input light 80 and a reflected light beam 104 and operates for directing input light beam 80 to light directing assembly 8 and directing reflected light beam 104 towards imaging assembly 110. Imaging assembly 110 includes an optional spectral filter 105, an imaging lens arrangement (e.g., tube lens) 106, and an imaging detector (camera) 107.

In order to enable switching between the measuring and imaging modes, mirror 73 is movable between its operative position being in input light path 71, thus enabling input light beam 80 propagation along the measurement channel, and its inoperative position being outside light path 71, thus allowing light beam 80 propagation along the imaging channel. The imaging channel operates as follows: Mirror 73 is shifted into its inoperative position; input light beam 80 passes through beam splitter 101, then passes through objective lens 103, and is focused on the wafer surface. Reflected light 104 returns back along the same optical path 71 towards beam-splitter 101, which reflects this beam 104 towards imaging lens arrangement 106, which focuses it on detector 107.

It should be noted that for the purpose of imaging, only a narrow spectral range (like visible or near IR) is usually needed, so all optical elements in the imaging channel might be relatively simple. In order to operate only with a required spectral range, spectral filter 105 can be used. Imaging detector 107 may be of any suitable known type, for example CCD, CMOS or the like. The electrical output of detector 107, in either analogue or digital form, is transferred to control system 6, which is configured and operable to process this signal in order to extract therefrom information about the required measurement site location relative to the measurement spot. This information is used to appropriately transfer stage 10 to bring the wafer to a required position for measurement.

In the present example of FIG. 2, the system utilizes the same illuminator for both the measurement and imaging channels. It should however, be noted that the imaging channel may utilize another illuminator within stationary assembly 110 using an additional beam splitter (not shown).

It should also be noted that beam-splitter 101 being permanently located in the measurement channel, might attenuate the light intensity in this channel. If such attenuation is undesirable, beam-splitter 101 may be movable between its operative position being in optical path 71 of beam 80 during the image acquisition, and an inoperative position being out of this path during the measurements.

It should also be noted that imaging tube lens 106 is used when objective lens 103 creates a collimated (infinity corrected) light beam. Since the distance between stage 10 (wafer) and imaging detector 107 is constant, imaging may be carried out by objective lens 103 only (conjugate imaging), and lens 106 may thus be omitted.

For precise imaging and measurements, a focus sensor (not shown) is usually needed in order to provide a control signal to the axis normal to stage 10 or alternatively to an optional vertical movement mechanisms (not shown) of objective lens 103, and thus provide the best focusing in each of the measurement and imaging channels. Such a focus sensor may be incorporated in the imaging channel, for example as disclosed in U.S. Pat. No. 5,604,344 assigned to the assignee of the present application.

The imaging arrangement may also be used for other purposes, for example as an additional measurement channel for the wafer angle measurements that might be needed when the wafer is not precisely flat, so the actual angle of incidence is different from the nominal value used for the data interpretation. One of the possible solutions is by calculating the wafer tilt angle by measuring defocus in different points of the imaging field of view. It is clear for persons skilled in the art that other solutions for the wafer angle measurement can be used as well, by means of the elements of the above-described imaging arrangement 110.

Figure 3:
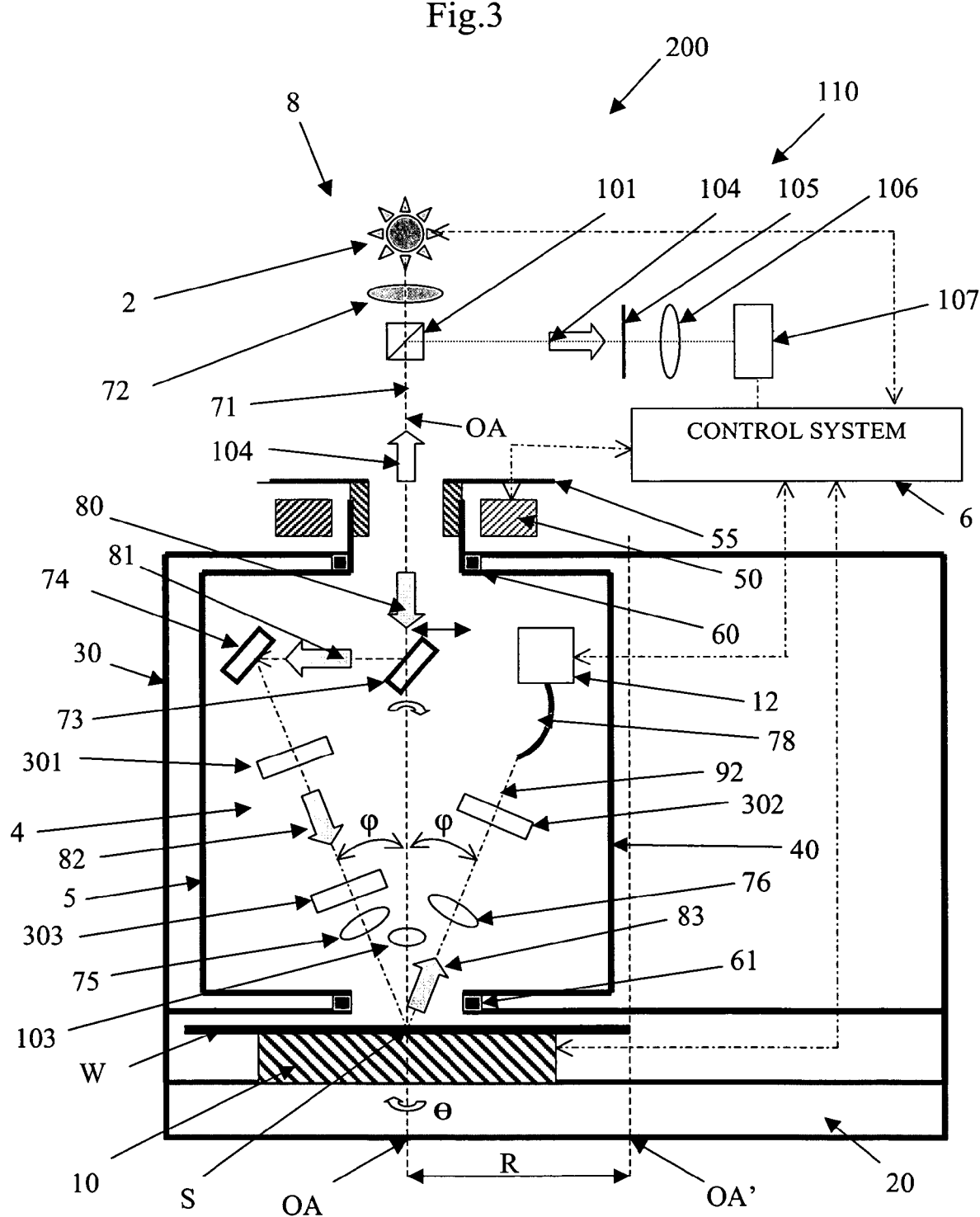
FIG. 3 shows schematically yet another example of a system of the invention defining measurement and imaging channels, where the measurement channel is configured to allow polarimetric or ellipsometric measurements.

Reference is made to FIG. 3, showing yet another example of a measurement system 200 according to the invention. System 200 is configured generally similar to the above-described system 100, namely defining measurement and imaging channels, but has a somewhat modified configuration of the measurement channel that allows polarimetric or ellipsometric measurements. To this end, a light directing assembly 8 also includes a polarization unit, which in the present example is formed by a polarizer 301 in a path of an incident beam reflected from mirror 74, an analyzer 302 is an optical path of a reflected beam 83, and an optional compensator 303 (phase retarder) which in the present example, is in an optical path of polarized incident beam 82 (but may be also located in optical path 83). Analyzer 302 and polarizer 301 may be of different types, for example Glan prism, Glan-Tompson prism and the like (disclosed for example in "Ellipsometry and Polarized Light, by R. M. Azzam et al., 1986) made of birefringent crystals like quartz, calcite, α-BBO and the like. At least one of analyzer 302 and polarizer 301 is preferably rotatable around an axis parallel to the respective light propagation path (91 for polarizer and 92 for analyzer).

By applying one of the well-known in the art techniques, such as rotating analyzer ellipsometry (RAE), Null-ellipsometry etc. (disclosed for example in "Ellipsometry and Polarized Light, by R. M. Azzam et al., 1986), it is possible to define polarization changes caused by the light reflection from a measurement site on wafer W. These ellipsometric parameters, usually termed ψ and Δ, may then be used, in parallel or instead of reflection coefficients measured by reflectometry, for the data interpretation.

The sensitivity of ellipsometric measurements can be increased by using compensator 303 either in the optical path of light emerging from polarizer 301, as shown in the figure, or in the optical path of returned light propagating towards analyzer 302. Such a compensator induces a phase shift between two orthogonal polarizations (for example, p- and s-components) enabling higher sensitivity. This can for example be useful when measuring in articles that generate very small phase shift by themselves (see for example "Ellipsometry and Polarized Light", by R. M. Azzam et al., 1986). The compensator may be a quarter-wave plate, Babinet-Soleil, Pockels or any other type suitable for a required spectral range.

The above-described oblique incidence system configurations are limited to one specific angle of incidence and reflectance θ between optical paths 91 (and 92) and the axis normal to the wafer surface. For many applications, e.g. spectral scatterometry, in order to obtain more information about the measured site, measurements with more than one incidence angle may be required.

Figure 4A:
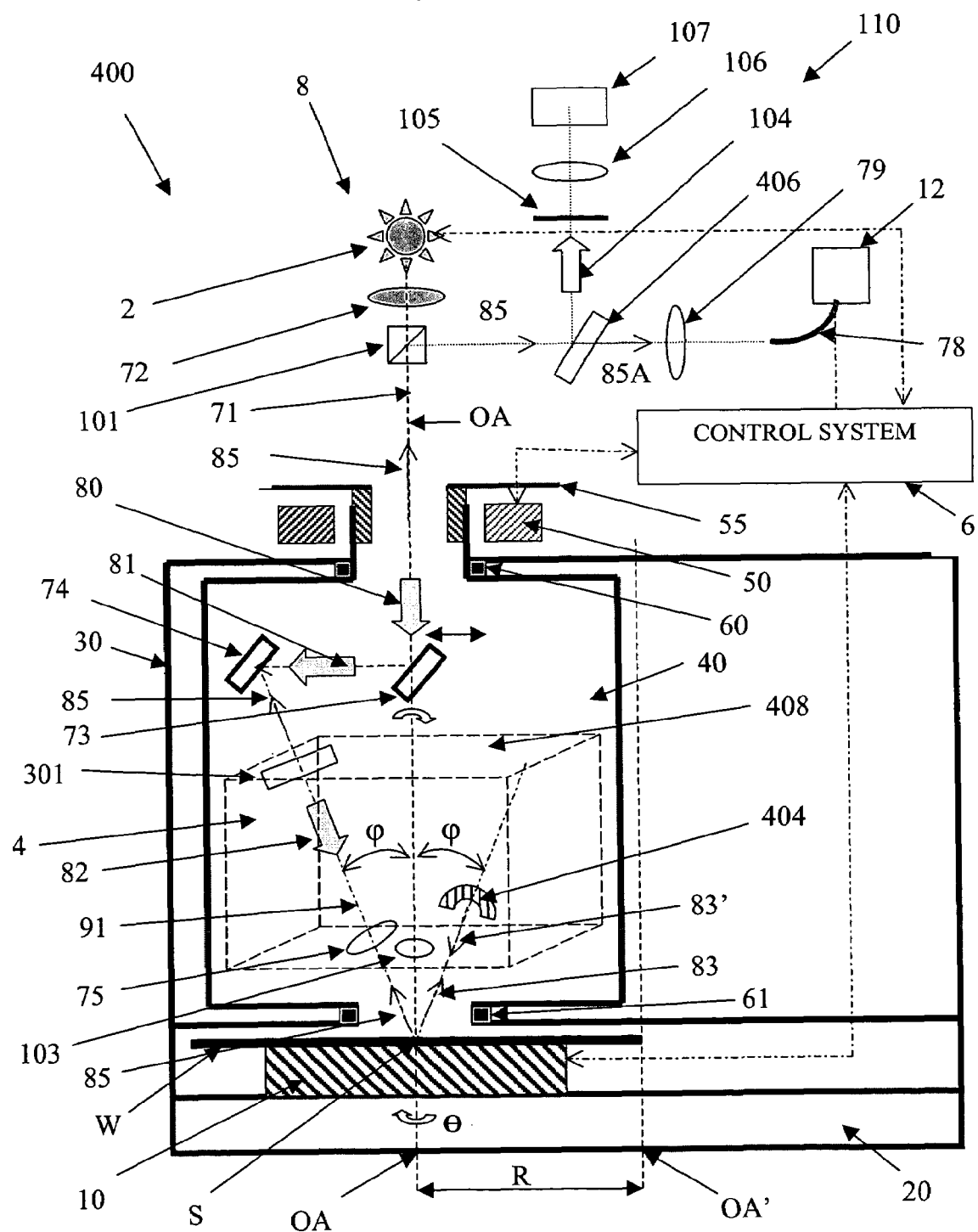
FIG. 4A schematically illustrates yet another example of a system of the invention utilizing the principles of a reverse ellipsometer, and configured to define an imaging channel and to operate with a small spot size.

Referring to FIG. 4A, there is schematically illustrated a monitoring system 400 according to yet another example of the invention. The system 400 configuration is based on the principles of a reverse ellipsometer (described in "A New Type of Precision Ellipsometer Without Employing a Compensator", by Masaki Yamamoto, pp. 200–202, Optics Communications, Vol. 10, No. 2, February 1974), but the system is implemented such as to operate with a small spot size and utilizes an imaging channel.

Such a reverse ellipsometer based scheme utilizes a light detector 12 located in the stationary part of the system, namely outside a rotating holder 40. This allows for using detectors without constrains of their size, weight, heat dissipation and electrical connections.

In system 400, a light directing assembly 408 includes a substantially spherical mirror 404 oriented to reflect a light beam 83 returned from a measurement spot S on wafer W towards the same spot. Hence, light is reflected twice from the same location on wafer W, thus enabling higher sensitivity to measured parameters, as compared to the schemes with one reflection only. Accordingly, a polarization unit includes a single polarizer 301 located in the optical path of both incident and returned light beams.

Thus, returned light beam 83 impinges onto mirror 404, and a reflected light beam 83' is incident onto the same spot, thus inducing a further returned light beam 85, which is collected by a lens 75, propagates through polarizer 301 and propagates towards a mirror 74. The latter reflects this beam 85 to mirror 73, which reflects it to a beam splitter 101, to be reflected towards detector 12. Accommodated upstream of detector 12 is a beam separator, e.g., pinhole mirror 406, which transmits a central part of this light beam 85A to detector 12 (via lens 79) and reflects a periphery part 104 of this light beam to an imaging assembly 110.

Comparing this double-reflection scheme with the ellipsometric scheme with single reflection and different polarizer and analyzer, the use of double reflection allows either higher sensitivity at the same angle of incidence or the same level of sensitivity, but at much lower angle of incidence, thus enabling significantly smaller spot size on the wafer.

Figure 4B:
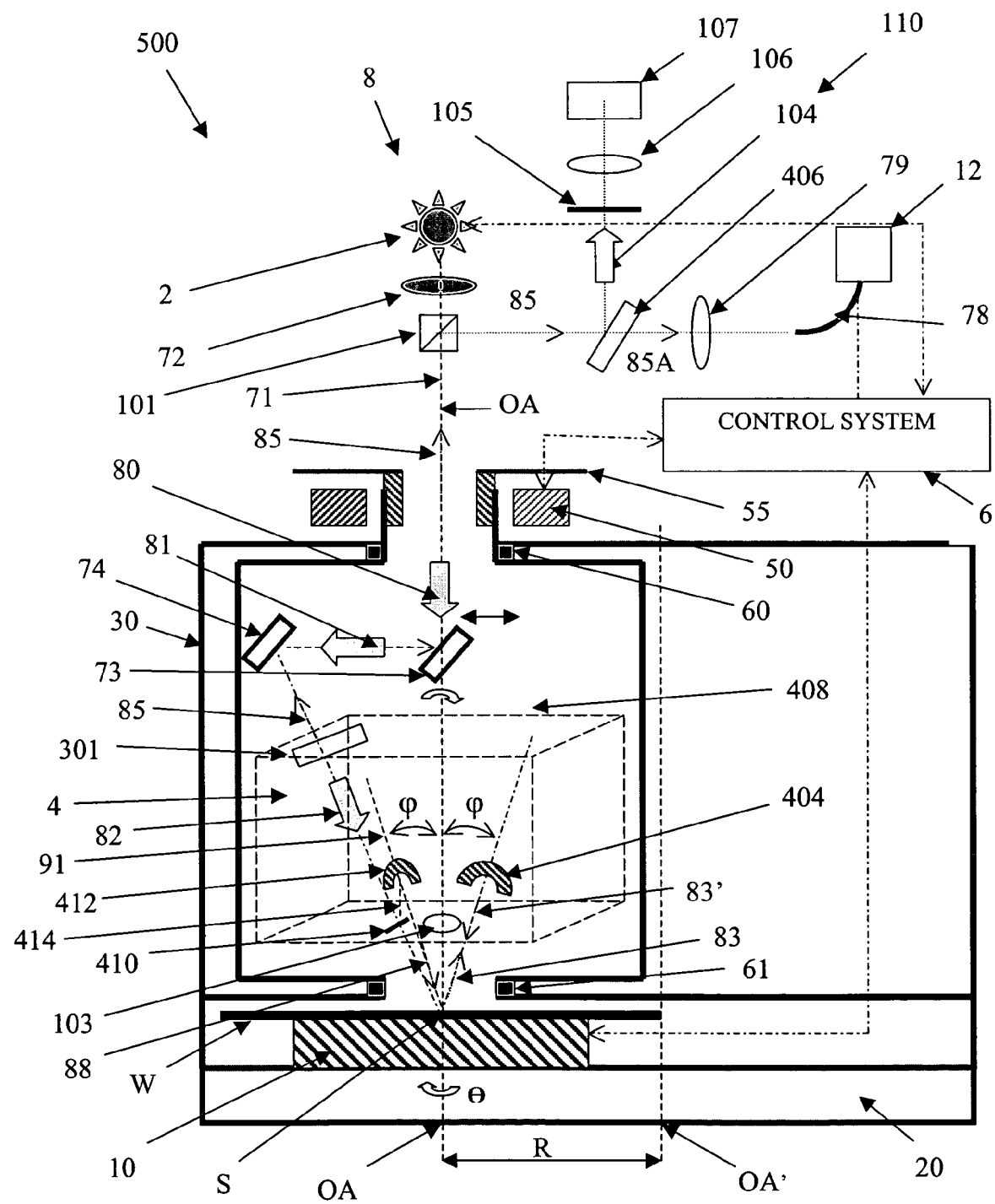
FIG. 4B is a schematic illustration of a system of the invention optimized for working with DUV illumination.

FIG. 4B schematically illustrates a system 500 configured generally similar to the above-described system 400, but optimized for working with DUV illumination. To this end, refractive focusing lens (75 in FIG. 4A) is replaced by a pair of reflective components—a plane mirror 410 and a concave mirror, e.g. spherical mirror 412. In this case, an illuminating light beam 82 impinges onto mirror 410 which reflects it along an axis 414 towards mirror 412. A light beam 88 reflected from mirror 412 propagates along an axis 91 and is focused onto a wafer W. A returned beam 83 is reflected by spherical mirror 404 to impinge onto the same spot on wafer W. A further returned beam 85 is reflected by spherical mirror 412 onto plane mirror 410 and is then reflected back to mirror 74. The configuration may be such that mirror 410 is apertured (has a hole) as described in U.S. application Ser. No. 11/003,012, assigned to the assignee of the present application, for transmitting the convergent beam 88 and returned beam 85. Since all the spherical mirrors reflect light substantially along their optical axes, their effect on light polarization is negligible.

As shown in FIGS. 4A and 4B, preferably all the components inside rotatable holder 40, except for mirrors 73 and 74, are located within a volume of a relatively narrow parallelepiped 408, for the purposes that will be described below.

It should be noted that pinhole mirror 406 actually presents a beam separator and may be replaced by a regular beam-splitter or the like, enabling optimal separation between the measurement and the imaging channels.

While the schemes of FIGS. 4A and 4B illustrate an ellipsometer, it should be understood that they may easily be modified to operate as a reflectometer.

It is appreciated that the system configurations described herein present specific but not limiting examples of an optical spectrometric system of the present invention configured to provide a rotating incidence plane. This enables creation of optical devices with several angles of incidence by utilizing most of common components. Examples of such devices, suitable to be used in any of the above-described system configurations, are shown schematically in FIGS. 5A–5C.

Figure 5A:
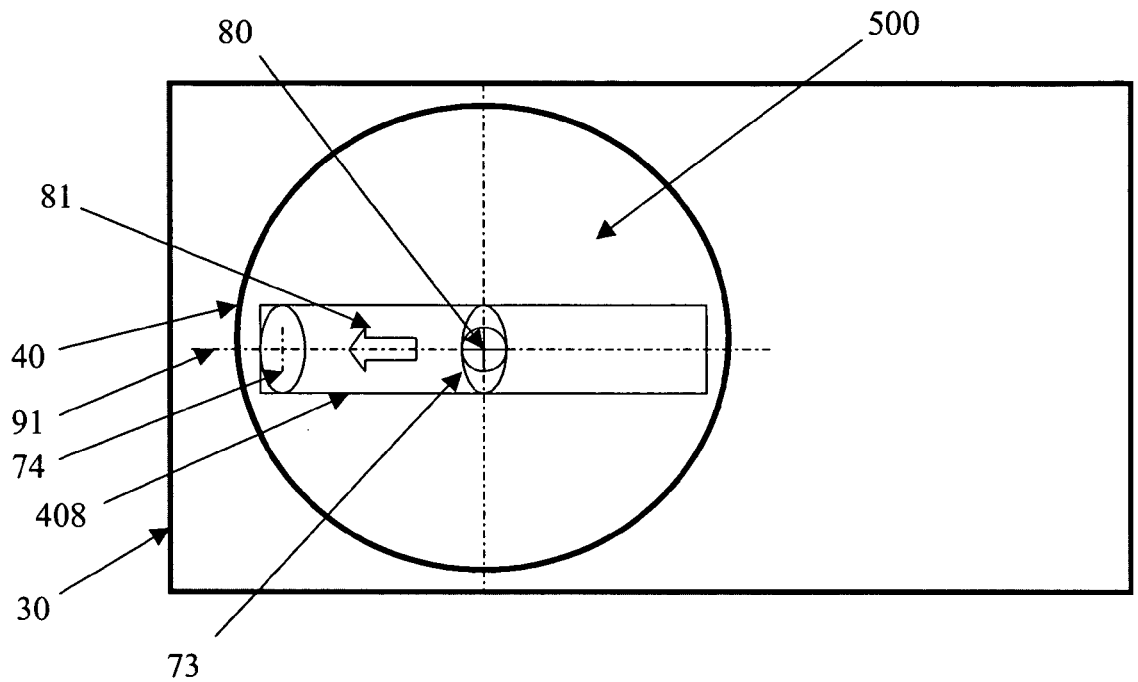
FIGS. 5A to 5C show three different examples, respectively, of an optical device suitable to be used in the system of the present invention to enable the system operation with several angles of incidence.

FIG. 5A shows partially a top view of an optical device 500 formed by elements downstream of a beam splitter (101 in FIGS. 2, 3 4A–4B). Here, only the elements needed for understanding of the device operation are shown, namely, mirrors 73 and 74 within a parallelepiped-like volume 408. An input light beam 80 is reflected by mirror 73, and a resulting light beam 81 is then reflected by mirror 74 to optical axis 91. The optical path after mirror 74 and back to a detector, as described above, and not shown here. It should be noted that parallelepiped 408 is relatively narrow in width, so it occupies a small part of the internal volume of the drum 40.

Figure 5B:
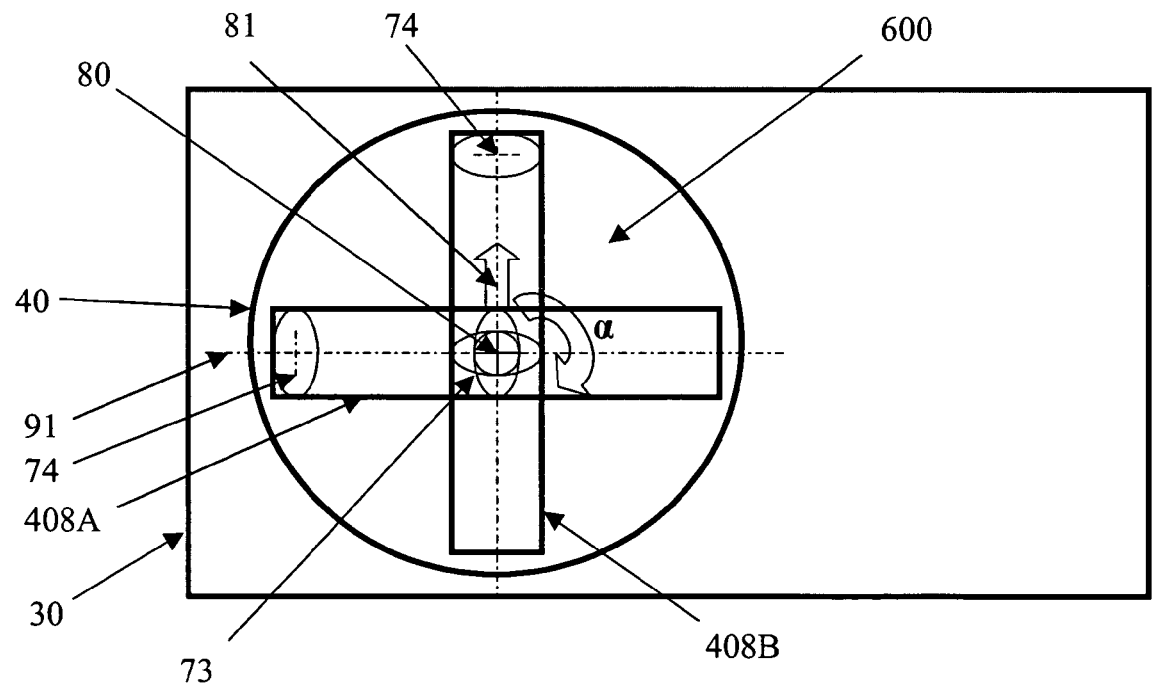

In the example of FIG. 5B, an optical device 600 is formed by two similar optical arrangements 408A and 408B located within a drum 40. In this example, the optical axes of these arrangements are perpendicular to each other. Each of arrangements 408A and 408B is configured generally similar to the above-described arrangement 408. The only difference between arrangements 408A and 408B is in the angle of incidence. For example, the angle of incidence $\phi_1$ provided by arrangement 408A is 40° while the angle of incidence $\phi_1$ provided by arrangement 408B is 50°. In order to operate both arrangements 408A and 408B, mirror 73 should enable two respective orientations relative to an input light beam 80, for example by rotation of mirror 73 on angle $\alpha$ relative to a drum 40. For this specific example of FIG. 5B, $\alpha$=90°. Instead of rotating mirror 73, any other suitable configuration of switching the input light beam from one optical axis to another may be used, e.g. by means of a movable slider consisting of two mirrors each oriented at a different angle relative to the drum axes.

Figure 5C:
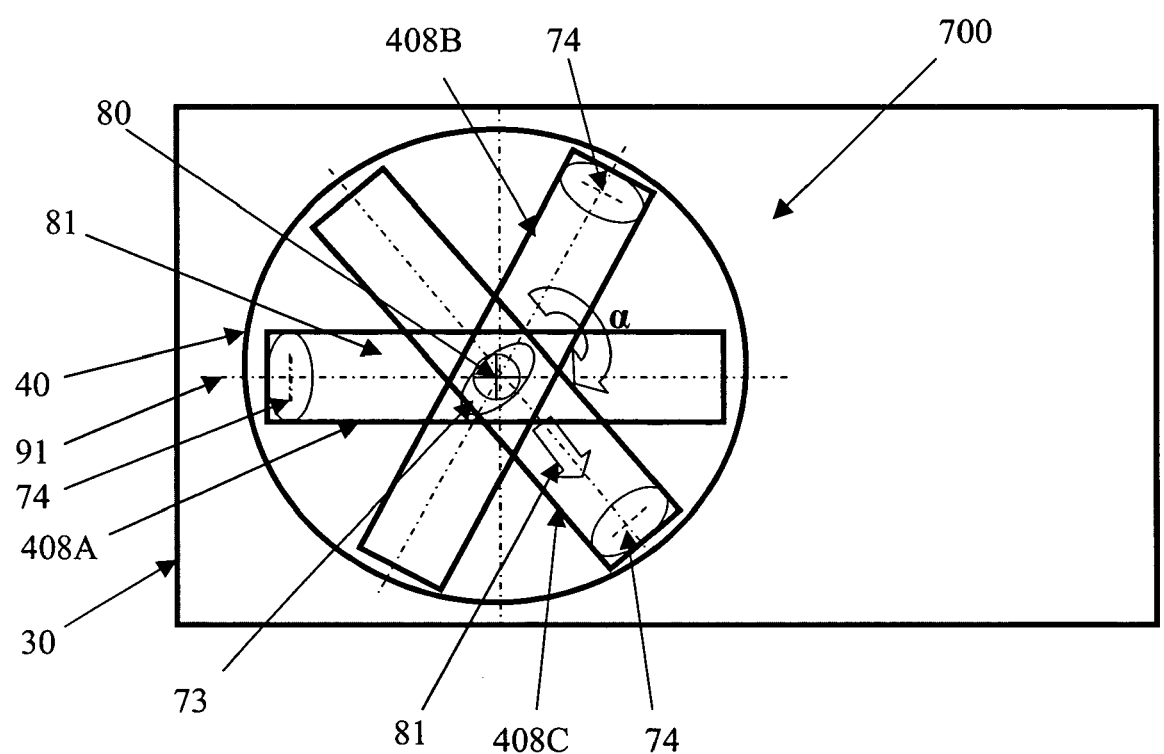

FIG. 5C shows yet another example of an optical device 700, but with three optical arrangements 408A, 408B and 408C, oriented at angle $\alpha$=120° with respect to each other, and each providing a different angle of incidence.

It is appreciated that a number of incidence angles may be higher than three. This depends on an available volume within drum 40 and volume of each optical device.

The optical devices illustrated in FIGS. 5A–5C enable optical measurements of any type, e.g. reflectometry, ellipsometry and the like at different incidence angles and a very small footprint of the entire system, which is at least in one dimension similar to the footprint of a wafer.

Using a system with rotating incidence plane provides for collecting optical measurement data not only for different wavelengths and different angles of incidence, but also at different azimuth angles, i.e., angle between the incidence plane and the measurement site orientation. This enables using a single compact system to collect maximum useful information for further interpretation of the required optical and geometrical parameters of the measured article.

While most of the examples illustrate optical spectrometric devices, it should be understood that the invention can be applied to other optical methods like laser ellipsometers, X-ray spectrometers, oblique imaging systems, etc.

Those skilled in the art will readily appreciate that various modifications and changes can be applied to the embodiments of the invention as hereinbefore exemplified without departing from its scope as defined in and by the appended claims.

The invention claimed is:

1. A system for measurement on an article, the system comprising:
   (i) an illuminator for producing light of at least one predetermined wavelength range;
   (ii) an optical system configured to define at least a measurement channel, the optical system comprising a light directing assembly for directing an illuminating light beam, propagating along an illuminating light path from the illuminator, onto a measurement site of the article, and directing a light beam returned from said measurement site to at least one light detector;
   (iii) a displacement arrangement associated with at least the light directing assembly of the optical system and configured and operable to rotate said at least light directing assembly of the optical system with respect to a stage supporting the article about a rotational axis substantially normal to the stage, thereby providing rotation of a light incidence plane relative to the article on the stage; and
   (iv) a control system configured and operable to control operation of said displacement arrangement.

2. The system of claim 1, wherein said stage is configured as an R-Theta stage operable by the control system.

3. The system of claim 2, wherein the displacement arrangement comprises a rotatable holder configured for holding said at least light directing assembly of the optical system.

4. The system of claim 3, wherein said rotatable holder is a hollow drum-like housing containing elements of the light directing assembly.

5. The system of claim 4, wherein the light detector is mounted in the drum.

6. The system of claim 4, wherein the light directing assembly comprises at least one optical device formed by a first folding reflector mounted on a central axis of the drum so as to be in said illuminating light path and at least one second folding reflector spaced-apart from the first reflector.

7. The system of claim 6, wherein the light directing assembly comprises an array of the optical devices formed by an array of the second folding reflectors arranged in a spaced apart relationship along a circumference of the drum all associated with the same first reflector, the system being therefore operable with variable angles of light incidence onto the measurement site.

8. The system of claim 3, wherein the light directing assembly is configured as a beam deflector assembly operable to provide a desired angle of incidence of the illuminating light beam onto the measurement site.

9. The system of claim 8, wherein the light directing assembly is accommodated so as to be orientable in the illuminating light path for deflecting the illuminating light beam towards the measurement site.

10. The system of claim 9, wherein the light directing assembly comprises a reflective unit which has one of the following configurations:
   (i) comprises a first folding mirror mounted so as to be orientable in said illuminating light path, and at least one second folding mirror accommodated so as to face by its reflective surface a reflective surface of the first folding mirror;
   (ii) comprises at least one total internal reflection prism for reflecting the illuminating light beam towards the measurement site;
   (iii) comprises a first folding mirror mounted so as to be orientable in said illuminating light path; at least one second folding mirror accommodated so as to face by its reflective surface a reflective surface of the first folding mirror; a substantially spherical mirror oriented to reflect the returned light beam towards the same measurement spot to induce a second returned light beam propagating towards said second folding mirror.
   (iv) comprises a first folding mirror mounted so as to be orientable in said illuminating light path; at least one second folding mirror accommodated so as to face by its reflective surface a reflective surface of the first folding mirror; a substantially plane mirror in a path of light reflected from the second folding mirror and propagating towards the measurement site; a first substantially spherical mirror oriented to reflect light, reflected from said substantially plane mirror, towards the measurement site and reflect returned light from the article onto said substantially plane mirror; and a second substantially spherical mirror oriented to reflect the returned light beam towards the same measurement spot to induce a second returned light beam propagating towards said first spherical mirror.

11. The system of claim 10, wherein the optical system comprises a beam separator unit accommodated in the light illuminating path to direct the illuminating light beam towards the light directing assembly and direct the returned light beam to said at least one light detector.

12. The system of claim 8, wherein the light directing assembly comprises a reflection unit comprising mirrors or at least one total internal reflection prism.

13. The system of claim 9, wherein the light directing assembly comprises at least one lens arrangement for carrying out at least one of focusing the illuminating light beam onto the measurement site; and collecting the returned light to direct it towards the light detector.

14. The system of claim 9, wherein the light directing assembly comprises a polarization unit accommodated to apply polarization rotation to the illuminating light beam and the returned light beam.

15. The system of claim 14, wherein the polarization unit comprises a polarizer accommodated in a path of the illuminating light beam deflected towards the measurement site, and an analyzer accommodated in the returned light beam path propagating towards the light detector.

16. The system of claim 15, wherein the polarization unit comprises a compensator accommodated either in a path of the polarized illuminating light propagating towards the measurement site, or in a path of the returned light propagating towards the analyzer.

17. The system of claim 15, wherein at least one of the polarizer and the analyzer is mounted for rotation around an axis parallel to the respective light path.

18. The system of claim 14, wherein the light directing assembly comprises a polarizer accommodated to apply polarization rotation to the illuminating light beam and said further returned light beam.

19. The system of claim 9, wherein the optical system is configured to define an imaging channel.

20. The system of claim 19, wherein the optical system comprises a beam separator unit accommodated in the light illuminating path outside the rotatable holder to direct the illuminating light beam towards the light directing assembly and to direct the returned light beam emerging from the light directing assembly to an imaging detector.

21. The system of claim 20, wherein the light directing assembly comprises a reflection unit comprising at least one reflector element which is displaceable between its operative position being in the light beam illuminating path and thus directing the illuminating light along the measurement channel and its inoperative position being outside the light illuminating path and thus allowing the illuminating light beam propagation along the imaging channel.

22. The system of claim 21, wherein the light directing assembly comprises an objective lens arrangement accommodated in a path of the illuminating light beam propagating along the imaging channel towards the article.

23. The system of claim 20, wherein the optical system comprises a second beam separator accommodated in a path of the returned light emerging from the first beam separator to direct first and second spatially separated portions of the returned light towards, respectively, the measuring and imaging detectors.

24. The system of claim 1, wherein the optical system comprises a light guide, highly reflective with respect to said at least one wavelength range, accommodated upstream of the light detector.

25. The system of claim 1, wherein the optical system is configured to define an imaging channel.

26. The system of claim 25, wherein the optical system comprises a beam separator unit accommodated in the light illuminating path to direct the illuminating light beam towards the light directing assembly and direct the returned light beam to an imaging detector.

27. A method for use in measurement on an article, the method comprising:
   (i) providing an illuminating light beam of at least one predetermined wavelength range, and directing the illuminating light beam along an illuminating light path;
   (ii) passing the illuminating light towards a measurement site through a deflector assembly rotatable with respect to the article about a rotational axis substantially normal to the article plane and configured to provide rotation of a light incidence plane relative to the article under measurements to provide a desired oblique angle of incidence of the illuminating beam onto the measurement; and (iii) directing a light beam returned from the article along an oblique return path to at least one light detector.

28. The method of claim 27, wherein said passing of the illuminating light through the deflector assembly comprises causing a double reflection of light from the same measurement site, thereby providing a certain level of sensitivity of measurements with a smaller spot size.

* * * * *